(12) United States Patent
Chang et al.

(10) Patent No.: US 11,364,139 B2
(45) Date of Patent: Jun. 21, 2022

(54) VARIABLE STIFFNESS DEVICES THAT USE THE PRINCIPLES OF GRANULAR JAMMING AND METHODS OF USE

(71) Applicant: Georgia Tech Research Corporation, Atlanta, GA (US)

(72) Inventors: Young-Hui Chang, Atlanta, GA (US); I-Ting Chuang, Atlanta, GA (US); Geza Frank Kogler, Atlanta, GA (US); Emily Simonds, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 494 days.

(21) Appl. No.: 16/298,214

(22) Filed: Mar. 11, 2019

(65) Prior Publication Data

US 2019/0274866 A1 Sep. 12, 2019

Related U.S. Application Data

(60) Provisional application No. 62/641,113, filed on Mar. 9, 2018.

(51) Int. Cl.
*A61F 5/32* (2006.01)
*A61F 5/34* (2006.01)
*A61F 5/14* (2022.01)

(52) U.S. Cl.
CPC ............... *A61F 5/32* (2013.01); *A61F 5/14* (2013.01); *A61F 5/34* (2013.01)

(58) Field of Classification Search
CPC ...... A61F 13/063; A61F 5/019; A61F 13/068; A61F 13/067; A61F 13/069; A61F 13/0246; A61F 13/102; A61F 5/0111; A61F 5/30; A61F 2013/00604; A61F 13/505; A61F 13/511; A61F 2013/0048; A61F 5/14; A61F 5/32; A61F 5/0195; A61F 5/34;

(Continued)

(56) References Cited

U.S. PATENT DOCUMENTS 5,288,286 A * 2/1994 Davis .................... A61F 5/0111
602/13
5,383,290 A * 1/1995 Grim ..................... A43B 7/147
36/44

(Continued)

FOREIGN PATENT DOCUMENTS

EP 0316289 A2 5/1989

*Primary Examiner* — Ophelia A Hawthorne
(74) *Attorney, Agent, or Firm* — Troutman Pepper Hamilton Sanders LLP; Ryan A. Schneider

(57) ABSTRACT

Embodiments of the present disclosure relate generally to variable stiffness devices, including orthoses, that use the principles of granular jamming. In some embodiments, a device may comprise a cell having an air impermeable outer bladder. The outer bladder of the cell can define an internal pocket. A plurality of granular particulates may be disposed within the first cell. The stiffness of the cell can be altered by altering the negative internal pressure of the cell, thereby causing the granular particulates to compact, or jam. In some embodiments, a plurality of cells may be disposed within a device. The location of each of the plurality of cells may correspond to a location of a user's foot. The mechanical characteristics of each cell of the plurality of cells may be independently adjusted by adjusting the negative internal pressure of the cell.

16 Claims, 10 Drawing Sheets

(58) Field of Classification Search
CPC ........... A43B 7/142; A43B 7/144; A43B 7/14;
A43B 7/141; A43B 13/12; A43B 7/1465;
A43B 7/1435; A43B 7/145; A43B
7/1495; A43B 13/40; A43B 13/42; A43B
23/07; A43B 13/188; A43B 7/148; A43B
17/006; A43B 21/28; A43B 23/0265;
A43B 13/386; A43B 3/108; A41B 11/00;
A41B 2400/322; A41B 2500/10
See application file for complete search history.

(56) References Cited

U.S. PATENT DOCUMENTS

| | | |
|---|---|---|
| 5,843,483 A | 12/1998 | Theriault et al. |
| 2007/0083995 A1* | 4/2007 | Purdy ................ A61G 7/05753 5/702 |

* cited by examiner

US 11,364,139 B2

VARIABLE STIFFNESS DEVICES THAT USE THE PRINCIPLES OF GRANULAR JAMMING AND METHODS OF USE

CROSS-REFERENCE TO RELATED APPLICATIONS

This Application claims priority to U.S. Provisional Patent Application No. 62/641,113, filed 9 Mar. 2018, which is hereby incorporated by reference herein in its entirety as if fully set forth below.

STATEMENT OF RIGHTS UNDER FEDERALLY SPONSORED RESEARCH

This invention was made with government support under grant number BCS0847325 awarded by the National Science Foundation. The government has certain rights in the invention.

FIELD OF THE DISCLOSURE

Embodiments of the present disclosure relate generally to variable stiffness devices that use the principles of granular jamming and, more particularly, to variable stiffness orthoses that use the principles of granular jamming.

BACKGROUND

Practitioners and orthosis companies alike design and manufacture orthotic devices to support, brace, and align various parts of the human anatomy. Over the years, these manufacturers have employed various materials and combinations of materials to optimize the mechanical properties of the orthotic devices. Optimizing the mechanical properties is important to provide proper support for whichever joint or limb is being supported. A common orthotic device is the orthotic insole for supporting and aligning the foot.

Many types of orthotic insoles exist in the market. Orthosis companies manufacture ready-to-wear orthotic insoles to address a variety of customer needs, including but not limited to needs such as shock absorption for athletic use, heel support, arch support, pronation support, and/or supination support. Practitioners create custom-made orthotic insoles to address a variety of patient needs, including but not limited to needs such as pressure relief for diabetic patients and pain relief for patients with plantar fasciitis. Regardless of whether current orthotic insoles are ready-to-wear or custom-made, the devices typically are manufactured using similar materials. These materials typically include a combination of plastics and foams.

Current methods of manufacturing ready-to-wear and custom-made orthotic inserts typically involve combining plastics and foams to create desired support, shock distribution, and pressure relief. For example, a single orthotic insole may comprise a stiff material at the hindfoot to support the heel and a less stiff material may be disposed at the forefoot to provide improved flexibility. Additionally, many layers of foams and plastics may be employed in a single orthotic insole to adjust the mechanical properties of the device. The heel support, for example, may include a plastic layer to improve stability, and the heel support may include a layer on top of the plastic layer to improve shock absorption. For customers and patients that rely on these devices for support and relief, a variety of challenges exist with the current foam-and-plastic compositions.

Ready-to-wear systems provide a limited number of orthosis combinations in which a customer may choose to purchase and wear. A customer with a particular need, for example, may be able to choose from a limited number of mass-produced orthoses for relief, but none may provide desired relief because the device is not custom-made for the patient. Additionally, a customer wishing to purchase an insole that is appropriate for running may be required to purchase a different insole for every-day use. Different uses can require different support at certain areas of the foot.

The vast number of potential uses for orthotic devices is also inhibitive for ready-to-wear systems. To capture all needs, a company may need to consider different levels of stiffness and/or softness at all areas of the foot. For a company to address every customer need, therefore, a company may need to design a device considering hindfoot support, forefoot support, midfoot (or arch) support, lateral support for supinators, medial support for pronators, etc. The combination of each of these areas means a company must manufacture hundreds of products to incorporate all potential customer needs.

For custom-made orthoses, a practitioner may manufacture an insole with different foams at different areas of the insole. A single insole, for example, may include stiffer material at areas of the foot where the patient needs extra support or energy absorption, and the insole may include a softer material at other areas of the foot for increased flexibility or comfort. In many cases, this means that an insole may comprise several types of foams throughout. This process can be prohibitively expensive because a practitioner must take the time to determine what level of support is needed at each area of the foot. Further, because the properties of these conventional devices (e.g., support, shock distribution, and pressure relief) cannot be adjusted after they are created, if the practitioner decides the device she created is not optimal for the patient, the insole must be discarded and the process starts again. This can increase the cost and wait time for the patient.

Finally, one undesirable trait found in both ready-to-use and custom-made orthoses is the material from which they are made. The foam materials used in currently-available orthoses comprise a densification strain. This is an area where, when stress is applied to the foam, the foam collapses upon itself and cannot recover to its original state. This is a significant issue for orthotic insoles, as a person's entire weight is applied to the device. The inherent problem with densification shows the foam may not be the optimal choice for orthotic insoles. What is needed, therefore, is a system that is customizable for the customer or patient, is customizable for different activities or needs, and is manufactured to avoid densification failure.

SUMMARY

Embodiments of the present disclosure address these concerns as well as other needs that will become apparent upon reading the description below in conjunction with the drawings. Briefly described, embodiments of the present disclosure relate generally to variable stiffness devices that use the principles of granular jamming and, more particularly, to variable stiffness orthoses that use the principles of granular jamming.

An exemplary embodiment of the present invention provides a system. The system may comprise a first cell having an air impermeable outer bladder. The outer bladder can define a first internal pocket containing a plurality of first granular particulates. The first cell may be configured to maintain a first negative internal pressure relative to an area external to the outer bladder. The system may further comprise a first valve in fluid communication with the first cell and the area external to the outer bladder. The first valve can extend from the first cell and through the outer bladder. The first valve may be configured to provide fluid flow into and from the first cell to adjust the first negative internal pressure.

In any of the embodiments described herein, the system may further comprise a second cell having an air impermeable outer bladder. The outer bladder can define a second internal pocket containing a plurality of second granular particulates. The second cell may be configured to maintain a second negative internal pressure relative to an area external to the outer bladder. The system may further comprise a second valve in fluid communication with the second cell and the area external to the outer bladder. The second valve can extend from the second cell and through the outer bladder. The second valve may be configured to provide fluid flow into and from the second cell to adjust the second negative internal pressure.

In any of the embodiments described herein, the first internal pocket may comprise a plurality of second granular particulates. The plurality of first granular particulates can be a different material than the plurality of second granular particulates.

In any of the embodiments described herein, the plurality of first granular particulates can be a different material than the plurality of second granular particulates.

In any of the embodiments described herein, the plurality of first granular particulates can comprise a different geometry than the plurality of second granular particulates.

In any of the embodiments described herein, the first negative internal pressure can be a different pressure than the second negative internal pressure.

In any of the embodiments described herein, the system can form part of an orthosis.

In any of the embodiments described herein, the system may further comprise a fluid pump. The fluid pump can be coupleable to the first valve. The system may further comprise a controller. The controller can be configured to operate the pump to adjust the first negative internal pressure to alter a stiffness of the first cell.

In any of the embodiments described herein, the system may further comprise a fluid pump that is coupleable to the first and second valves. The system may further comprise a controller configured to operate the pump to adjust the first negative internal pressure to alter a stiffness of the first cell. The controller may further be configured to operate the pump to adjust the second negative internal pressure to alter a stiffness of the second cell.

Another exemplary embodiment of the present invention provides a method. The method may comprise providing a user-orthosis interface. The interface may comprise a first cell having an air impermeable outer bladder, the first cell containing a plurality of first granular particulates. The interface may further comprise a first valve in fluid communication with the first cell and an area external to the outer bladder, the first valve extending from the first cell and through the outer bladder, and wherein the first valve is configured to provide fluid flow into and from the first cell. The method may further comprise providing a pressure controller configured to attach to the first valve and provide fluid into and remove fluid from the first cell to adjust a first internal pressure of the first cell. The method may further comprise removing fluid, via the pressure controller, from the first cell to decrease the first internal pressure. The method may further comprise causing the plurality of first granular particulates to compact with each other to increase a stiffness of the first cell.

In any of the embodiments described herein, the interface may further comprise a second cell having an air impermeable outer bladder, the second cell containing a plurality of second granular particulates. The interface may further comprise a second valve in fluid communication with the second cell and an area external to the outer bladder, the second valve extending from the second cell and through the outer bladder, and wherein the second valve is configured to provide fluid flow into and from the second cell. The pressure controller may be further configured to attach to the second valve and provide fluid into and remove fluid from the second cell to adjust a second internal pressure of the second cell. The method may further comprise removing fluid, via the pressure controller, from the second cell to decrease the second internal pressure. The method may further comprise causing the plurality of second granular particulates to compact with each other to increases a stiffness of the second cell.

In any of the embodiments described herein, the stiffness of the first cell can be greater than the stiffness of the second cell.

In any of the embodiments described herein, the plurality of first granular particulates can be a different material than the plurality of second granular particulates.

In any of the embodiments described herein, the plurality of first granular particulates can comprise a different geometry than the plurality of second granular particulates.

In any of the embodiments described herein, the interface can be part of an orthotic insole. The orthotic insole can be disposed within a shoe.

In any of the embodiments described herein, the interface can be part of an orthotic insole. The orthotic insole can be disposed within a shoe, and the shoe can comprise a first end and a second end. The first cell can be proximate the first end of the shoe, and the second cell can be proximate the second end of the shoe.

Another exemplary embodiment of the present invention provides a method. The method may comprise providing an orthotic insole. The orthotic insole may comprise a first cell having an air impermeable outer bladder, the outer bladder defining a first internal pocket containing a plurality of first granular particulates. The orthotic insole may further comprise a first valve providing fluid communication between the first internal pocket and an area external to the first cell. The method may further comprise providing a pressure controller coupleable to the first valve. The method may further comprise removing fluid, via the pressure controller, from the first cell to decrease a first internal pressure in the first cell relative to the area external to the first cell, wherein decreasing the first internal pressure causes the plurality of first granular particulates to compact and increases a stiffness of the first cell.

In any of the embodiments described herein, the orthotic insole may further comprise a second cell having an air impermeable outer bladder, the outer bladder defining a second internal pocket containing a plurality of second granular particulates. The orthotic insole may further comprise a second valve providing fluid communication between the first internal pocket and an area external to the second cell. The pressure controller can be coupleable to the second valve. The method may further comprise removing fluid, via the pressure controller, from the second cell to decrease a second internal pressure in the second cell relative to the area external to the second cell, wherein decreasing the second internal pressure causes the plurality of second granular particulates to compact and increases a stiffness of the second cell.

In any of the embodiments described herein, the stiffness of the first cell can be greater than the stiffness of the second cell.

In any of the embodiments described herein, the plurality of first granular particulates can be a different material than the plurality of second granular particulates.

In any of the embodiments described herein, the orthotic insole and the pressure controller can both be disposed within a shoe.

These and other aspects of the present disclosure are described in the Detailed Description below and the accompanying figures. Other aspects and features of embodiments of the present disclosure will become apparent to those of ordinary skill in the art upon reviewing the following description of specific, example embodiments of the present disclosure in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the disclosure discussed herein. In similar fashion, while example embodiments may be discussed below as device, system, or method embodiments, it is to be understood that such example embodiments can be implemented in various devices, systems, and methods of the present disclosure.

BRIEF DESCRIPTION OF THE FIGURES

Reference will now be made to the accompanying figures and diagrams, which are not necessarily drawn to scale, and wherein.

DETAILED DESCRIPTION

Figure 1:
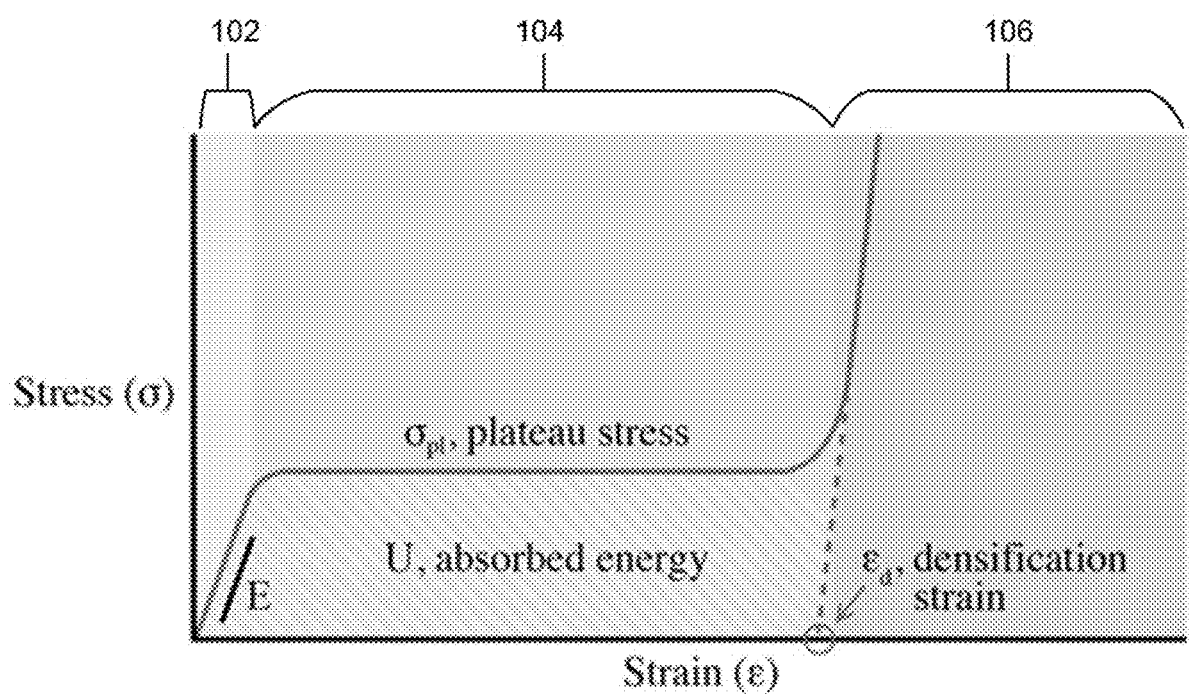
FIG. 1 is a graph showing a stress-strain curve for exemplary foams used in traditional orthotic devices.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

It should also be noted that, as used in the specification and the appended claims, the singular forms "a," "an" and "the" include plural references unless the context clearly dictates otherwise. References to a composition containing "a" constituent is intended to include other constituents in addition to the one named.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter. Additionally, the components described herein may apply to any other component within the disclosure. Merely discussing a feature or component in relation to one embodiment does not preclude the feature or component from being used or associated with another embodiment.

To facilitate an understanding of the principles and features of the disclosure, various illustrative embodiments are explained below. In particular, the presently disclosed subject matter is described in the context of being devices, including orthoses, that use the principles of granular jamming to achieve desired mechanical properties. The present disclosure, however, is not so limited and can be applicable in other contexts. Some embodiments of the present disclosure may improve the functionality of other devices that may benefit from variable stiffness, including but not limited to custom seating and/or prosthetic limb sockets. Additionally, although various embodiments described herein refer to orthotic insoles, it will be understood by those having skill in the art that other orthotic devices can benefit from the systems and methods described herein. For example and not limitation, the principles described in the present disclosure can improve upon orthotic devices for the foot, the knee, the elbow, the hip, or any other joint where an orthosis may be employed. These embodiments are contemplated within the scope of the present disclosure. Accordingly, when the present disclosure is described in the context of being devices, including orthoses, that use the principles of granular jamming to achieve desired mechanical properties, it will be understood that other embodiments can take the place of those referred to.

As described above, current design and manufacturing methodologies for foot orthoses involve iterative and time-consuming processes that can introduce potentially detrimental errors in fit, support, function, or any combination thereof. An orthosis is generally designed for a specific purpose based on factors such as the expected rate and magnitude of loading. The properties of these conventional orthoses (e.g., support, shock distribution, and pressure relief) cannot be adjusted after they are manufactured. Thus, patients and consumers alike may require multiple orthoses to accommodate different activities of daily life. A single consumer, for example, may need one orthosis for athletic activities and a different orthosis for day-to-day support.

Not only are current foot orthoses lacking in terms of multi-use customizability, the materials from which they are manufactured also add to the devices' limitations. Current systems employ various combinations of plastics and foams. These materials are positioned about the orthosis in a manner so as to adjust the mechanical properties of the orthosis at various locations, i.e., foams often provide a cushioning effect such that the peak pressures on certain areas of the foot are reduced and redistributed. For example, a stiffer foam may be positioned at the heel of an orthosis to increase stability, energy absorption, and/or shock distribution, and another area of the foot may provide less stiff material to increase the softness.

Significantly, for practitioners that create custom-made orthoses, this means manually selecting foams of different stiffness, volume, thickness, and/or density for certain areas of the orthoses, cutting the foam for that area, and then layering the foam on other layers of foam to create the zones of support needed for the patient. Not only is this process laborious and expensive, if the practitioner decides any given layer of foam is not created as intended for the patient, an entirely new orthosis must be created, thus increasing the amount of labor for the practitioner and cost for the patient.

Another, and a significant, limitation with current orthoses is the material characteristics of the foams used in the devices. The mechanical behavior of a foam is very different from the behavior of solid materials. Cell wall bending in foams has ramifications that are evident when examining its mechanical response to loading. FIG. 1 is a graph showing a stress-strain curve for exemplary foams used in traditional orthotic devices. As shown in the graph, initially, foam behaves linearly and elastically. In this linear region 102, foam has an elastic modulus, E. This modulus is valid until foam's elastic limit, characterized by cell walls yielding or buckling. The material then enters a second region 104, where the foam can be compressed at a near constant stress, called the plateau stress. A third region 106 begins when the cell walls within the foam collapse to a point of densification, preventing the walls from collapsing any further. At this point, mechanical stress rises rapidly. The densification strain is considered a critical strain where the material begins to fail and cannot recover to its original state. Densification is common for foam orthotic insoles, as a person's entire body weight is applied to the foam material over numerous cycles.

The present disclosure provides a novel orthotic system that solves the problems associated with current systems. In particular, embodiments of the present disclosure describe variable stiffness orthoses that use the principles of granular jamming. Granular jamming refers to a material phase transition where a fluid-like granular medium (e.g., sand, rice, beads, etc.) can become rigid by adjusting the control conditions (e.g., density), such that there is no appreciable flow. As described herein, a wide range of configurations are possible for an orthosis that uses the principles of granular jamming. The ability to adjust material properties of the orthotic device through vacuum pressure allows for a single orthotic device to suit a wide range of desirable applications and activities. Additionally, and as will be described in more detail herein, orthoses employing the principles of granular jamming do not show the densification failures found in foam orthotic devices.

Throughout this disclosure reference is made to the "stiffness" of a product. It will be understood that the stiffness of a material relates to an amount of energy absorption and shock distribution for the material. Energy absorption describes how much energy a given material can dissipate when force is applied. A material that is less stiff can absorb and dissipate less energy but is a softer material. The stiffer the material is, the greater the capacity for energy absorption and shock distribution. Therefore, when reference is made to stiffness of a material, it will be understood that this refers also to energy absorption and shock distribution of the material.

As will be appreciated, other material properties of a device may change when particulates are jammed within an orthotic device. For example, a higher degree of jamming (i.e., compaction) of the particulates within an orthotic device may also increase the failure strain, decrease the wear of the product over time, and/or increase the elasticity of the orthotic device over time.

Various devices and methods are disclosed for providing variable stiffness orthoses that use the principles of granular jamming, and exemplary embodiments of the systems and methods will now be described with reference to the accompanying figures.

Figure 2A:
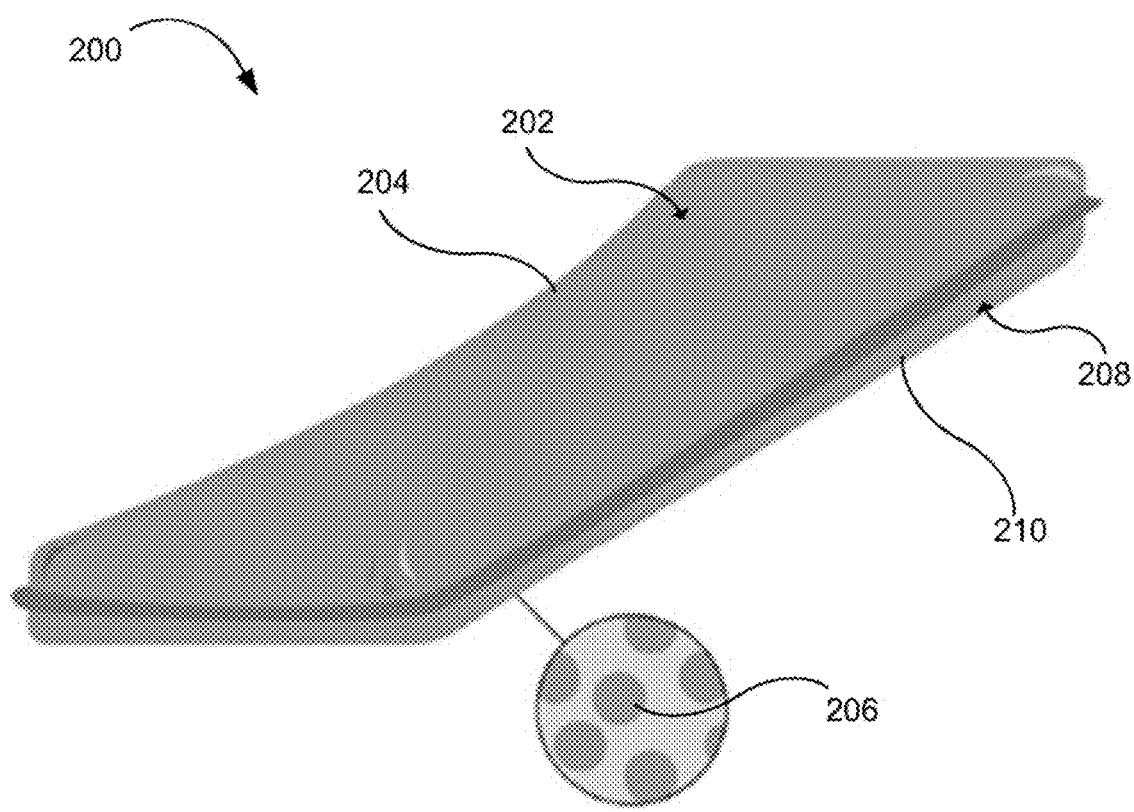
FIG. 2A depicts an exemplary variable-stiffness orthotic device having a cell and an outer bladder, wherein the device is not compressed, according to an exemplary embodiment of the present disclosure.
Figure 2B:
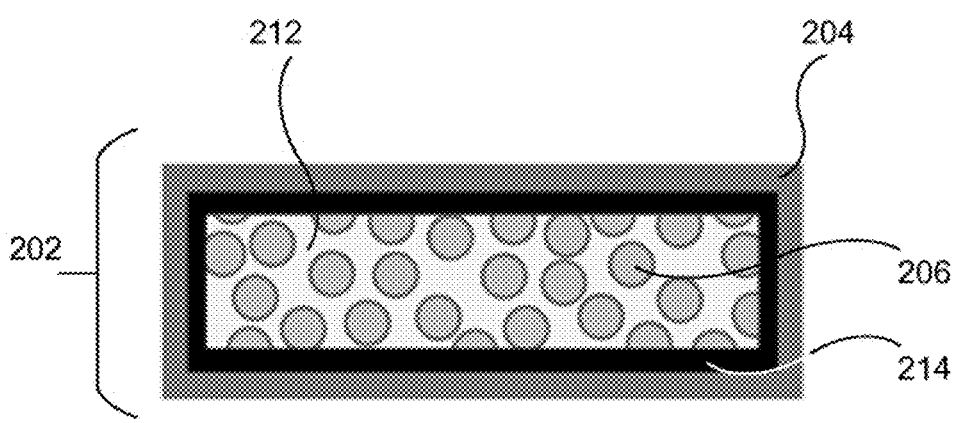
FIG. 2B is a cross-sectional view of an exemplary variable-stiffness orthotic device having a cell and an outer bladder, wherein the particulates are not jammed, according to an exemplary embodiment of the present disclosure.

FIGS. 2A and 2B depict an exemplary variable-stiffness orthotic device 200, according to an exemplary embodiment of the present disclosure. FIG. 2A depicts an exemplary variable-stiffness orthotic device 200 having a cell 202 and an outer bladder 204, according to an exemplary embodiment of the present disclosure. In some embodiments, a variable-stiffness orthotic device 200 may comprise a cell 202. In some embodiments, the cell 202 has an air impermeable outer bladder 204 surrounding the cell 202. The outer bladder 204 can define an internal pocket within the cell 202. As will be described in greater detail herein, the outer bladder 204 may be air impermeable, as an air impermeable outer bladder 204 may allow the internal pocket within the cell 202 to maintain a defined pressure relative to the pressure outside of the outer bladder 204. In some embodiments, the outer bladder 204 may comprise a plastic sheet material including but not limited to polyvinyl chloride, neoprene, silicone rubber, polyurethane, Cuben fiber, polyurethane coated nylon, or any combination thereof. As will be appreciated by those having skill in the art, other air impermeable sheets or membranes may be used with the presently disclosed systems.

In some embodiments, the cell 202 may contain a plurality of particulates 206. The particulates 206 may be granular particulates that remain fluid-like when flowing freely, but become rigid when their density increases, i.e., space between the particulates 206 is removed and the particulates 206 compact with each other. It is the compacting, or jamming, of the particulates 206 that causes the material properties of the cell 202 to change. As will be described in more detail herein, providing different particulates 206 within a cell 202 may change the mechanical properties of the cell 202 once the particulates 206 are compacted. It is contemplated that a cell 202 may comprise one type of particulate 206 or multiple types of particulates 206. In an example device having multiple types of particulates 206 within a cell 202, the material composition of any two types of particulates 206 may be different, the geometry of any two types of particulates 206 may be different, or any combination thereof. It is contemplated that the particulates 206 may be sand, rice, plastic beads, poppyseeds, coffee grinds, or any similar macroscopic particle, as will be appreciated.

In some embodiments, a variable-stiffness orthotic device 200 may comprise a second cell 208, wherein the second cell 208 defines an internal pocket within the second cell 208. The second cell 208 (or any additional cell) may be disposed at any location on the orthotic device 200. FIG. 2A depicts an example orthotic device 200 wherein the second cell 208 is disposed parallel to the other cell 202 within the orthotic device 200, which is in accordance with some embodiments. In such an embodiment, the stiffness of the second cell 208 may be adjusted independent of the other cell 202, this achieved by adjusting the pressure within one cell 202, 208 to a different internal pressure than the other cell 208,202. An example of this would be an orthotic device 200 with one level of stiffness along the bottom surface of the device 200, and then another level of stiffness at the arch surface (i.e., the top of the device). Other embodiments are contemplated, and various other embodiments are described herein or will become apparent upon reading the disclosure in conjunction with the figures.

The second cell 208 may comprise an outer bladder 210. The outer bladder 210 may be similar to the outer bladder 204 described above in the discussion for the aforementioned cell 202. In some embodiments, the material composition of the outer bladder 210 of the second cell 208 may be the same material composition as the outer bladder 204 of the first cell 202. In other embodiments, the outer bladders 204,210 may comprise a different material composition. The material compositions, for example, may be optimized for the intended characteristics of the cell. For example and not limitation, an outer bladder 204,210 that is resting adjacent to the wearer's foot may be more resistant to moisture, while an outer bladder 204,210 that is resting against the sole of a shoe may be more durable or flexible. Any combination of the materials described herein may be used for any outer bladder 204,210 described herein. In some embodiments, two or more cells 202,208 may be enclosed by a single outer bladder. In such embodiments, the cells may comprise a dividing layer disposed between the cells. The dividing layer may comprise the same or a different material than the outer bladder.

In some embodiments, a second cell 208 may comprise a plurality of particulates 206. The particulates 206 disposed within a second cell 208 may be any of the particulates 206 described herein. It is contemplated that a second cell 208 may comprise one type of particulate 206 or multiple types of particulates 206. In an example device having multiple types of particulates 206 within a second cell 208, the material composition of any two types of particulates 206 may be different, the geometry of any two types of particulates 206 may be different, or any combination thereof. In some embodiments, the particulates 206 of the second cell 208 may be different, either in material composition, geometry, or both, than the particulates 206 in the additional cell 202. As will be described in greater detail herein, different particulates may provide different mechanical characteristics when subject to varying degrees of jamming, and the different characteristics may be beneficial at different locations of the orthotic device 200, i.e., different locations of the foot.

In some embodiments, any cell 202,208 described herein may comprise an internal volume within the pocket of the cell 202,208. The internal volume may also be altered to adjust the material characteristics of the device. For example, a greater volume may be employed to fill the cell 202,208 with a greater number of particulates 206. This may correspond to altering the thickness of the orthotic device 200. The volume of particulates within a cell 202 may also correspond to the energy absorption (or stiffness) of the material. It is contemplated that the volume of any cell 202,208 may be from between 200 ml and 700 ml. The volume of a cell 202,208 may be outside of this range in some embodiments, as the volume may be adjusted based on the size of the insole, for example to accommodate larger or smaller shoe sizes.

The invention described herein contemplates many variations and modifications of the orthotic device 200, including using alternative geometries of structural elements, combining shapes and structural elements from various example embodiments, using alternative materials, etc. Therefore, when any feature is defined in relation to a particular cell, it will be understood that any cell may comprise that feature. Additionally, a first cell may comprise some of the features described for a cell, and a second cell may comprise the same or different features. These embodiments are contemplated in the present systems.

In any of the embodiments described herein, an orthotic device 200 may be shaped to fit a particular use. For example, the exemplary embodiment shown in FIG. 2A depicts a rectangular device. Although a rectangular orthotic device 200 is in accordance with some embodiments, other shapes are contemplated. A common use case is that the shape of the orthotic device 200 is not rectangular but instead shaped as an insole, wherein the insole may be inserted into or manufactured within a shoe.

FIG. 2B is a cross-sectional view of an exemplary variable-stiffness orthotic device 200 having a cell 202 and an outer bladder 204, according to an exemplary embodiment of the present disclosure. FIG. 2B depicts an embodiment having a cell 202 defining an internal pocket 212, the internal pocket 212 containing a plurality of particulates 206. In some examples, a cell 202 may comprise an inner bladder 214. The inner bladder 214 may be disposed between the outer bladder 204 and the particulates 206. In some embodiments, the inner bladder 214 may be air-permeable. An air-permeable inner bladder 214 may allow air between the particulates 206 to be evacuated and may prevent particulates 206 from exiting the internal pocket 212 of the cell 202 (e.g., through a valve, which will be discussed in greater detail herein). As will be appreciated, the inner bladder 214 may comprise any material that allows fluid flow into and out of the cell, and the material may include but is not limited to nylon fabric. As can be seen in the figure, the particulates 206 in the cell 202 of FIG. 2B are non-compacted. In the present illustration, therefore, the particulates 206 remain fluid-like and are not jammed into their semi-solid-like form.

Figure 3A:
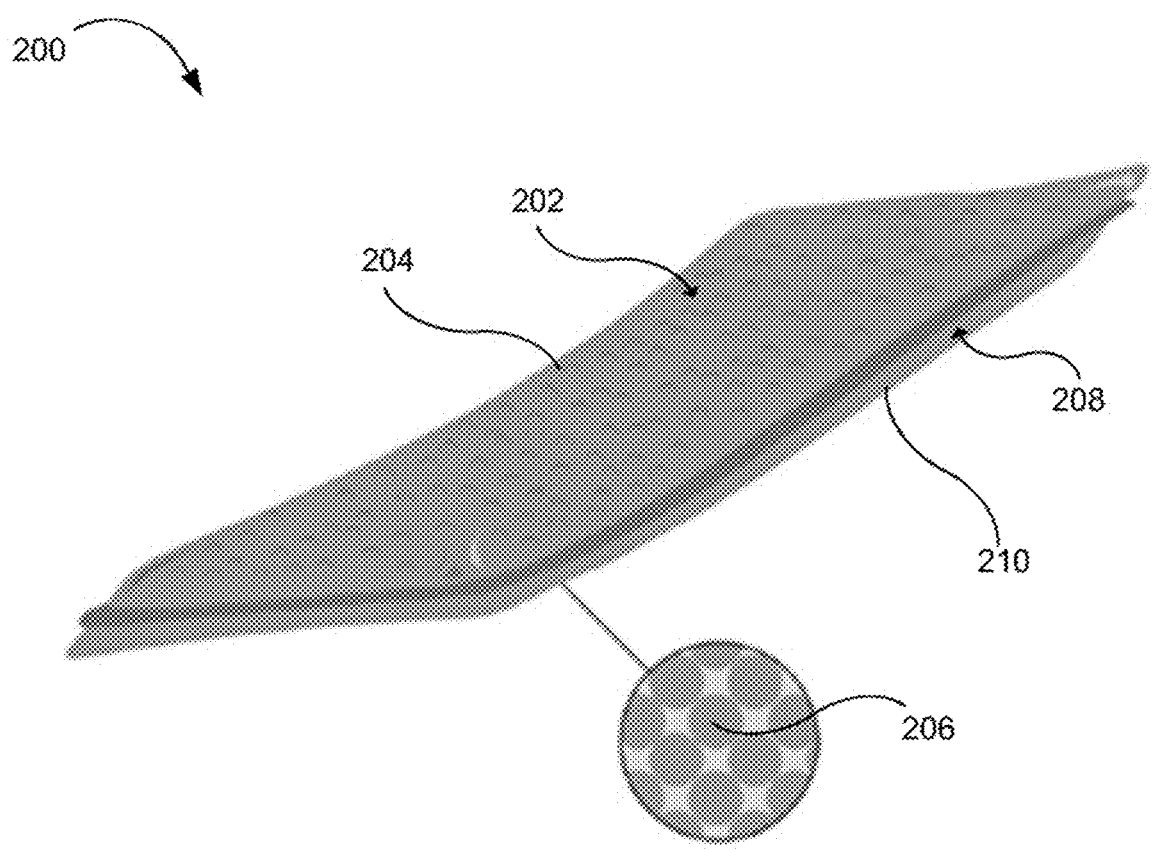
FIG. 3A depicts an exemplary variable-stiffness orthotic device having a cell and an outer bladder, wherein the device is compressed, according to an exemplary embodiment of the present disclosure.
Figure 3B:
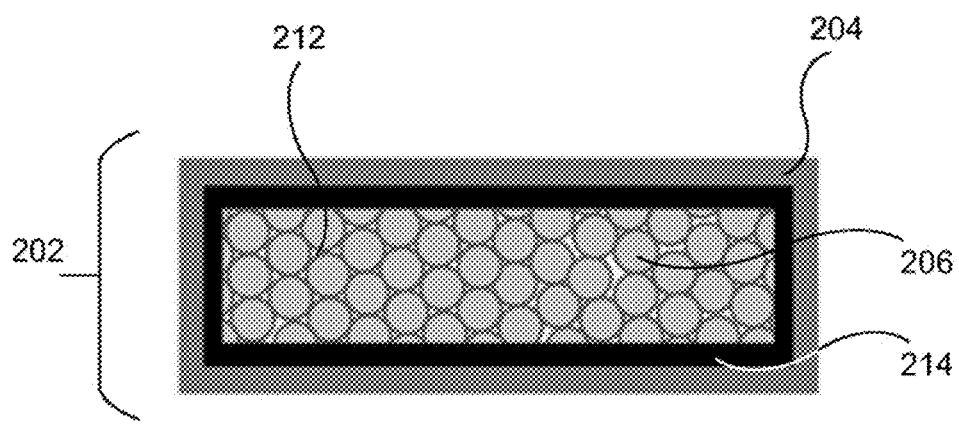
FIG. 3B is a cross-sectional view of an exemplary variable-stiffness orthotic device having a cell and an outer bladder, wherein the particulates are jammed, according to an exemplary embodiment of the present disclosure.

FIGS. 3A and 3B depict an exemplary variable-stiffness orthotic device 200, wherein the particulates 206 are compacted by a negative internal pressure of the cell 202, according to an exemplary embodiment of the present disclosure. FIG. 3A depicts a similar example orthotic device 200 as the device 200 found in FIG. 2A, according to an exemplary embodiment of the present disclosure. As can be seen, once the fluid within the internal pocket of the cell 202 has been removed, the particulates 206 become compacted, or jammed, together. This jamming creates the semi-solid-like structure in which the present invention employs. As will be described in greater detail herein, the jamming of particulates 206 increases the stiffness, which includes an increase in energy absorption and shock distribution. These mechanical properties are directly related to the type of particulate disposed within the cell 202,208 and the internal pressure of the cell 202,208.

FIG. 3B is a cross-sectional view of an exemplary variable-stiffness orthotic device 200 having a cell 202 and an outer bladder 204, according to an exemplary embodiment of the present disclosure. FIG. 3B depicts an embodiment having a cell 202 defining an internal pocket 212, the internal pocket 212 containing a plurality of particulates 206. As can be seen, once the fluid within the internal pocket 212 of the cell 202 has been removed, the particulates 206 become compacted, or jammed, together.

Figure 4:
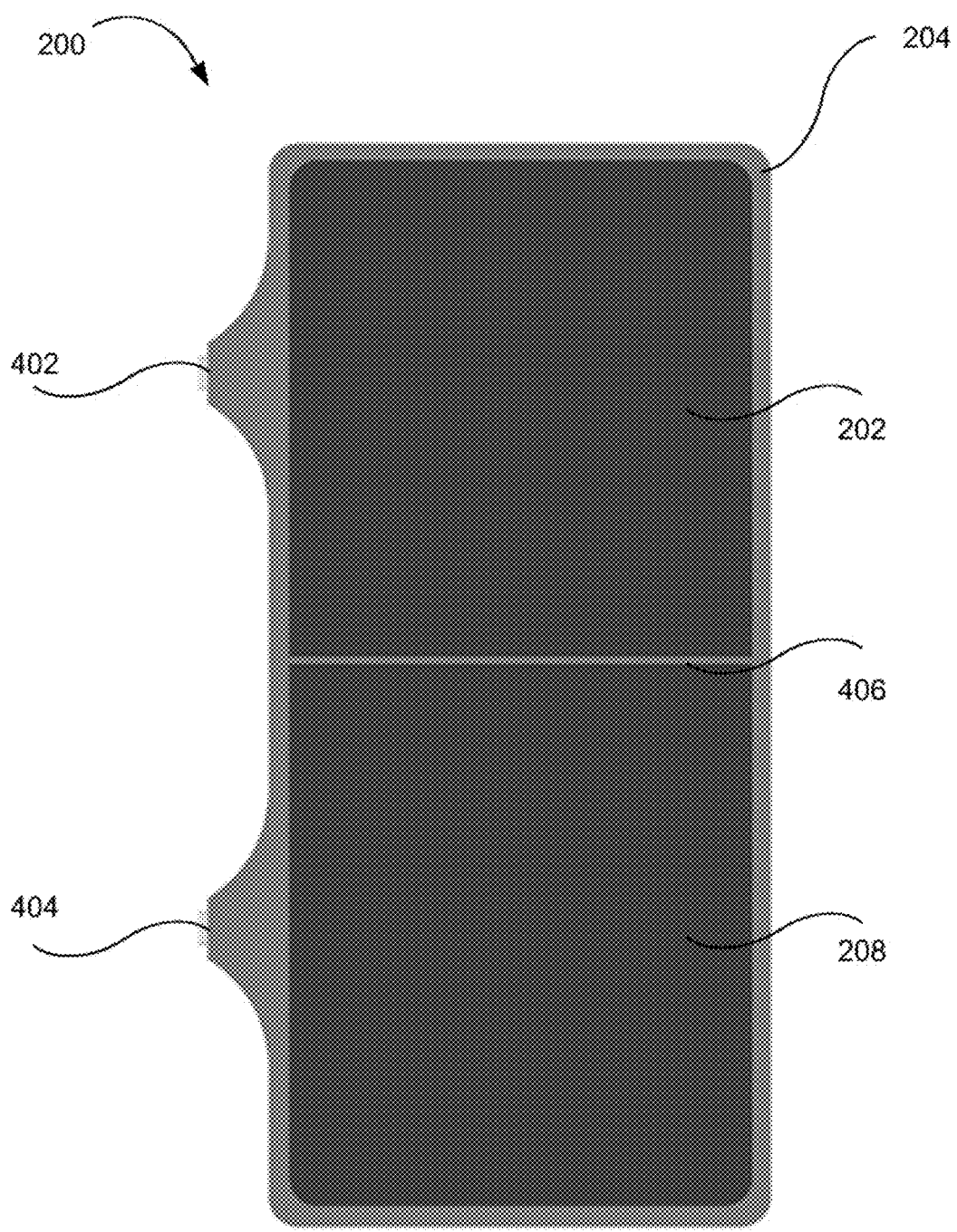
FIG. 4 depicts an exemplary variable-stiffness orthotic device having a first cell, a second cell, and a valve for each cell, according to an exemplary embodiment of the present disclosure.

FIG. 4 depicts an exemplary variable-stiffness orthotic device 200 having a first cell 202, a second cell 208, and a valve 402,404 for each cell, according to an exemplary embodiment of the present disclosure. As described above, any orthotic device 200 described herein may comprise one cell or a plurality of cells. A cell may be disposed in parallel layers, as shown in FIGS. 2A-3B. In other embodiments, cells may be disposed in different areas across the surface of the orthotic device 200. In FIG. 4, the exemplary orthotic device 200 comprises a first cell 202 at one end of the device and a second cell 208 at a second end of the device, which is in accordance with some embodiments of the present disclosure. In the example embodiment shown in FIG. 4, the material properties of the first cell 202 may be adjusted independent of the material properties of the second cell 208. This may be accomplished by any of the methods described herein. For example, a first cell 202 may comprise the same or a different type of particulate (not shown in FIG. 4) than a second cell 208. In some embodiments, the first cell 202 may comprise a first volume of particulates, and the second cell 208 may comprise a second volume of particulates; the first volume and the second volume may be the same or be different, depending on the use of the device. Additionally, the material properties of the first cell 202 may be adjusted independent of the second cell 208 by adjusting the internal pressure of each cell 202,208 independently, thereby adjusting the compaction, or jamming, of the particulates with each individual cell 202,208. For example and not limitation, if a first cell 202 is positioned about the heel of a person, the first cell 202 may be adjusted to be stiffer, absorb more energy, and distribute more energy across the surface of the cell 202; and if a second cell 208 is positioned in the forefoot, the second cell 208 may be adjusted to be less stiff. As will be appreciated by those having skill in the art, other configurations may be desired, and the other configuration are possible with the present systems.

In any embodiment described herein, a cell 202,208 may comprise a valve 402,404. In some embodiments, a valve 402,404 may extend from a cell 202,208 and through the outer bladder 204. In some embodiments, a valve 402,404 may be in fluid communication with a cell 202,208 and the area external to the outer bladder 204. A valve 402,404 may provide fluid flow, e.g., air, into and from a cell 202,208 to adjust the internal pressure within the cell 202,208. A valve may comprise tubing extending from the internal pocket of a cell 202,208 and through the outer bladder 204. In some embodiments, a valve 402,404 and/or tubing extending through the outer bladder 204 may comprise a filter (not shown in the figure). The filter may be disposed at a position so as to prohibit particulates within the cell 202,208 from exiting the internal pocket of the cell 202,208. This would be an alternative embodiment to the inner bladder 214 previously discussed. In some embodiments, a device 200 may comprise neither an inner bladder 214 nor a filter; in some embodiments a device 200 may comprise both.

In some embodiments, the orthotic device 200 may comprise a plurality of valves, each valve associated with a cell 202, 208. For example, FIG. 4 depicts an orthotic device having a first cell 202 and a second cell 208, and the device 200 comprises a first valve 402 associated with the first cell 202 and a second valve 404 associated with the second cell 208. This is in accordance with some embodiments of the present disclosure. As will be described in greater detail herein, more valves may be provided in a device having more than two cells.

A valve 402,404 can maintain an internal pressure within a cell 202,208. For example, if the fluid, e.g., air, within a cell 202,208 is removed so that the particulates within the cell 202,208 become jammed, the valve 202,208 can maintain the negative internal pressure of the cell 202,208 relative to the area external to the outer bladder 204. It is contemplated that the valve is able to maintain this internal pressure. A valve 402,404 can be many different types of valves, including, but not limited to, a self-sealing plastic balloon valve, a Schrader valve, a Presta valve, a Boston valve, a military valve, a pinch valve, a rubber ball valve, an inflatable toy valve, a stopcock valve, a Luer stopcock valve, and the like. In some embodiments, a single cell 202,208 may comprise more than one valve 402,404. For example, some embodiments may include a plurality of valves 402, 404 at any single cell 202,208 such that the fluid may be provided into and removed from a cell 202,208 with multiple different tools or mechanisms. As will be appreciated, different valves 402,404 are coupleable to different pressure controllers.

As described above, a first cell 202 and a second cell 208 may each comprise separate outer bladders joined together where the two cells 202,208 meet. In some embodiments, the device 200 may comprise a single outer bladder 204, and the two cells 202,208 may comprise a dividing layer 406 between the cells to separate the internal pockets of the cells. Either configuration is contemplated. The same configurations are possible when more than two cells are disposed within a single orthotic device 200.

Figure 5:
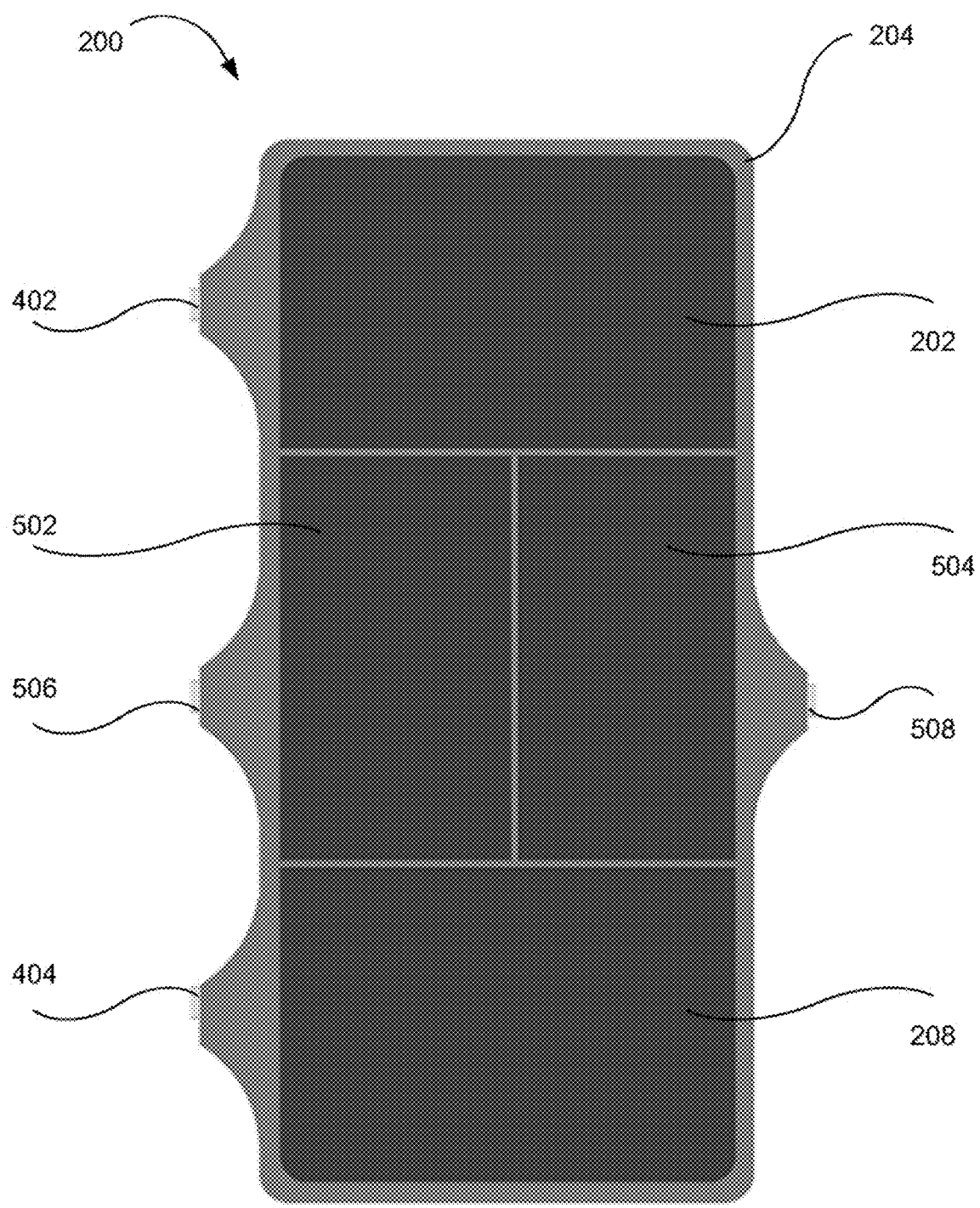
FIG. 5 depicts an exemplary variable-stiffness orthotic device having a plurality of cells and valves, according to an exemplary embodiment of the present disclosure.

FIG. 5 depicts an exemplary variable-stiffness orthotic device 200 having a plurality of cells 202,208,502,504 and valves 402,404,506,508, according to an exemplary embodiment of the present disclosure. As described herein, an orthotic device 200 may comprise any number of cells. FIG. 5 depicts an orthotic device 200 comprising four cells 202,208,502,504, which is in accordance with some embodiments of the present disclosure. An individual cell 202,208, 502,504 may be disposed at various positions in the foot, and the material properties of each cell may be adjusted independent of each other cell by adjusting the internal pressure of each cell independently. By adjusting the internal pressure of each cell independently, the particulates within each cell may be compacted, or jammed together, in varying degrees.

In some embodiments, a cell may be disposed at positions on the orthotic device 200 to address particular user needs. For example, a first cell 202 may be disposed near the forefoot, a second cell 208 may be disposed near the hindfoot, a third cell 502 may be disposed near the medial arch, and a fourth cell 504 may be disposed near the lateral arch. As described herein, by adjusting the internal pressure, and therefore particulate jamming, of each of these cells 202,208,502,504, the material properties of each cell may be adjusted independently. This may allow a device 200, for example, to have a greater stiffness (energy absorption and shock distribution) at the heel and lateral arch, and a lower stiffness at the medial arch and forefoot. Any other combination of material properties for the plurality of cells 202, 208,502,504 is possible with the present systems. Therefore, a single orthotic device 200 may be manufactured, and numerous iterations of support can be created with the single orthotic device 200.

In some embodiments, the cells 202,208,502,504 of an orthotic device 200 may be square or rectangular, as shown in FIG. 5. In some embodiments, the cells 202,208,502,504, as seen from the top or the bottom of the orthotic device 200, can comprise other shapes. For example, a first cell 202 may be disposed at a hindfoot portion of the orthotic device 200, and the first cell 202 may comprise a rounded perimeter so as to correspond to the shape of a heel. The perimeter of any other cell within an orthotic device 200 may be rounded or curved, and the shape of the cell 202,208,502,504 may depend on the placement of the cell 202,208,502,504 with respect to the user's anatomy.

In some embodiments, an orthotic device 200 may comprise any number of cells. For example, although FIG. 5 depicts an embodiment with four cells 202,208,502,504, other embodiments are contemplated, and the individual cells may be disposed in the orthotic device 200 at any number of foot regions. The embodiments shown in the present disclosure are merely exemplary and are not limiting. In some embodiments, each cell 202,208,502,504 may comprise a corresponding valve 402,404,506,508. Each valve 402,404,506,508 may comprise any of the features for any of the valves described herein.

Figure 6:
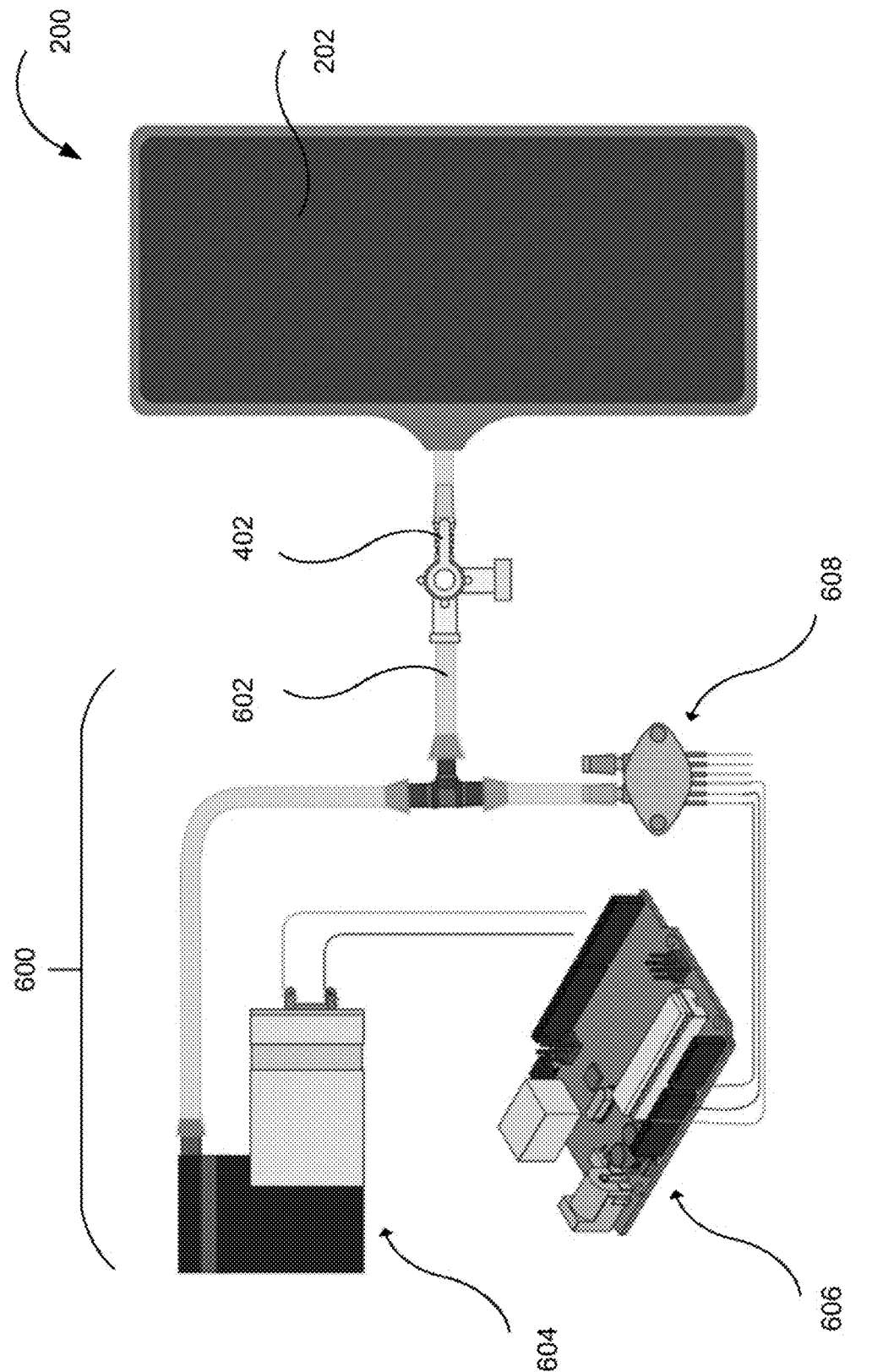
FIG. 6 depicts an exemplary pressure controller connected to an orthotic device, according to an exemplary embodiment of the present disclosure.

FIG. 6 depicts an exemplary pressure controller 600 connected to an orthotic device 200, according to an exemplary embodiment of the present disclosure. In some embodiments, a pressure controller 600 may be provided in a system to adjust the mechanical properties of a cell 202. In some embodiments, a pressure controller 600 may comprise a couple 602 that connects, i.e., couples, to a valve 402 of an orthotic device 200.

In some embodiments, a pressure controller 600 may comprise a fluid pump 604. A fluid pump 604 may be coupleable to an orthotic device 200 at a valve 402 of the orthotic device 200. In some embodiments, a fluid pump 604 may be an electronic vacuum pump that may be operated by a power source. In some embodiments, a fluid pump 604 may be a manually-operated pump, for example a hand pump. In some embodiments, the vacuum range of a fluid pump 604 may be in the range of from between of 0 kPa to −50 kPa. As will be described in greater detail herein, exemplary embodiments of an orthotic device 200 were tested at a pressure of −20 kPa, which is in accordance with some embodiments. In other embodiments, the volume range of the fluid pump may be less than from between 0 kPa to −50 kPa. For example, a hand pump may provide a vacuum range less than −50 kPa (i.e., somewhere between 0 kPa and −50 kPa). Smaller vacuum ranges are, therefore, contemplated. In some embodiments, the fluid pump 604 may remove air from the internal pocket of a cell 202. It is also contemplated that the present systems may incorporate other fluids, such as liquids, within each cell 202. In these embodiments, the fluid pump 604 may remove the alternative fluid from the cell 202.

In some embodiments, a pressure controller 600 may comprise a microcontroller 606 and/or a pressure sensor 608. A microcontroller 606 and/or a pressure sensor 608 may monitor the pressure within a cell 202. Although it is not necessary that the pressure controller 600 monitor the negative pressure within a cell, some embodiments may benefit from monitoring the pressure in cell 202. For example and as described herein, in an embodiment with a plurality of cells disposed in the orthotic device 200, the material properties of each individual cell may be adjusted according to the desired properties for that particular cell. A microcontroller 606 and/or a pressure sensor 608 may be designed to provide a feedback to tell the user of the systems the level of internal pressure for each cell. In such an embodiment, a user may know the individual stiffness level for each cell.

In some embodiment, a pressure controller 600 may be a separate system that is coupleable to an orthotic device 200. In some embodiments, the pressure controller 600 and the orthotic device 200 may be incorporated into a single system. For example, it is contemplated that an orthotic device 200 and a pressure controller 600 may be incorporated into a shoe. In such an embodiment, the fluid pump 604 for adjusting the internal pressure of a cell 202 may be disposed within the shoe. It is contemplated that a user can adjust the material characteristics of the orthotic device 200 directly on the shoe.

Experimental Section

The following section discusses experiments performed on exemplary orthotic devices. The experiments evaluated the effect of varying the particulate material, particulate volume, and internal negative pressure of the orthotic device.

Four design constraints were considered for an orthotic device: the ability of the system to (i) maintain a desired air pressure for an extended duration, (ii) adjust air pressure to various levels, (iii) sense the internal pressure, and (iv) rebound to the device's original shape and dimension after the pressure is reset.

The experimental set-up comprised two subsystems: a bladder/valve system and a pressure control system. The orthotic device comprised two rectangular bladders (108× 273 mm): an internal breathable bladder made from nylon fabric and an airtight outer bladder made from polyvinyl chloride sheet. The breathable inner bladder was provided to allow the air between the inner granular particulates to be evacuated and to prevent granular particulates from clogging the tubing. The inner bladder was filled to a specified volume with granular particulates and then sewn shut. The air-impermeable outer bladder was sealed around the inner bladder, along with the external tubing and a valve. The valve chosen for the experimentation was a stopcock valve. The orthotic device was detachable from the pressure controller system once the desired vacuum level was achieved and the stopcock valve closed. The orthotic devices comprised a single cell.

As particulate material affects the flow mechanics, packing density, viscosity, and yield stress of the aggregate system, three different granular media were chosen to investigate the effects of the size, shape, and material of the granular particulates on orthosis function: polystyrene beads, poppyseeds, and rice. Polystyrene beads were selected as the primary granular medium because they are lightweight and compliant on the scale of an individual granule, are readily available, and are cost effective. Polystyrene beads were used to test the effects of volume fill (Small: 300-325 ml, Medium: 375-400 ml, Large: 450-500 ml) and granule size. Three exemplary devices were filled with microbeads having a diameter of 1.2 mm, and three exemplary devices were filled with beads having a diameter of 4.4 mm. Poppyseeds and rice were used to test the behavior of stiffer granular materials of different sizes. One exemplary device was filled with poppyseeds having a diameter of approximately 0.8 mm, and one exemplary device was filled with rice having a length of approximately 5 mm and a width of approximately 2 mm.

To determine if the orthotic devices could mimic the energy absorption characteristics of a range of commercially available foams, the internal pressure for each prototype was altered to tune its density and, in turn, its material properties. To alter the internal pressure, a pressure controller system was provided. The pressure system comprised a microcontroller to control the system. A vacuum with a range of 0 to −50 kPa applied a negative pressure to the orthosis, and the pump was connected to the microcontroller using a motor shield. A pressure sensor was provided to monitor the internal pressure of the orthosis, the pressure sensor having a maximum error value of 2.5% over a temperature range of 0 to 85° C. The pump was attached via a clear tubing (3/16" or 4.7 mm diameter) to a three-way barbed fitting. The other barbed fitting was connected to the orthosis via a medical stopcock valve. A custom code controlled the microcontroller to maintain the desired pressure within the orthosis.

The main focus of testing was the material's performance under compression, as this is the loading condition primarily experienced by a foot orthosis. ASTM D1621-16 and D3575-14 standards were followed and modified to reflect the prototypes' limitations due to its dimension and thickness. The rectangular prototype dimensions approximated a US 10.5 men's shoe size, which provides a representative volume that corresponds to a typical foot orthosis. The thicknesses of the specimens (both commercial and prototypes under vacuum) were all within the range of common orthosis thicknesses (~6-19 mm, or ~0.25-0.75 in.), but were smaller than those of the standards; therefore, a slightly lower deflection (10%) ensured that the custom-sized test plates did not contact during testing. As densification failure was not observed for the orthosis prototypes, a second crush protocol was developed to specifically examine the failure strain of the prototypes. Other test parameters remained unchanged with the exception of the deflection magnitude, which reached values of approximately 22%.

A mechanical test machine with a controller and data acquisition software performed the monotonic uniaxial compression tests. Tests were performed at room temperature (20-21° C.) and atmospheric pressure. Displacement control was used to collect data at constant strain rates of 0.001 s$^{-1}$ and 0.1 s$^{-1}$. Strain was measured using an extensometer, which was accurate to ±0.00127 cm (0.0005 in). It was calibrated at a range of strains with no significant hysteresis between −10% strain and 2.5% strain, the working range of the experiment. Each sample (both commercial and prototype) was tested to 10% deflection. Time, force, displacement, and strain data were collected during testing. Eighty tests were conducted on eight granular orthosis protypes prototypes and fourteen tests were conducted on seven commercially-available foam materials.

The energy absorption, U, was calculated as the area under the stress-strain curve from onset of the test to densification strain (as shown in FIG. 1) for each foam sample and granular orthosis prototype. The foams tests were limited by their densification. In contrast, the granular orthosis did not reach a failure point during the standard testing protocol. Energy absorption for the granular orthosis prototypes was therefore calculated twice, once with a limit equal to the minimum measured foam densification strain (0.011), and once with the maximum foam densification strain measured (0.067). This calculation gave two values: (1) the granular orthosis' energy absorption with respect to the failure bounds of the most compliant foam and (2) its energy absorption with respect to the failure bounds of the stiffest foam.

Results

Figure 7B:
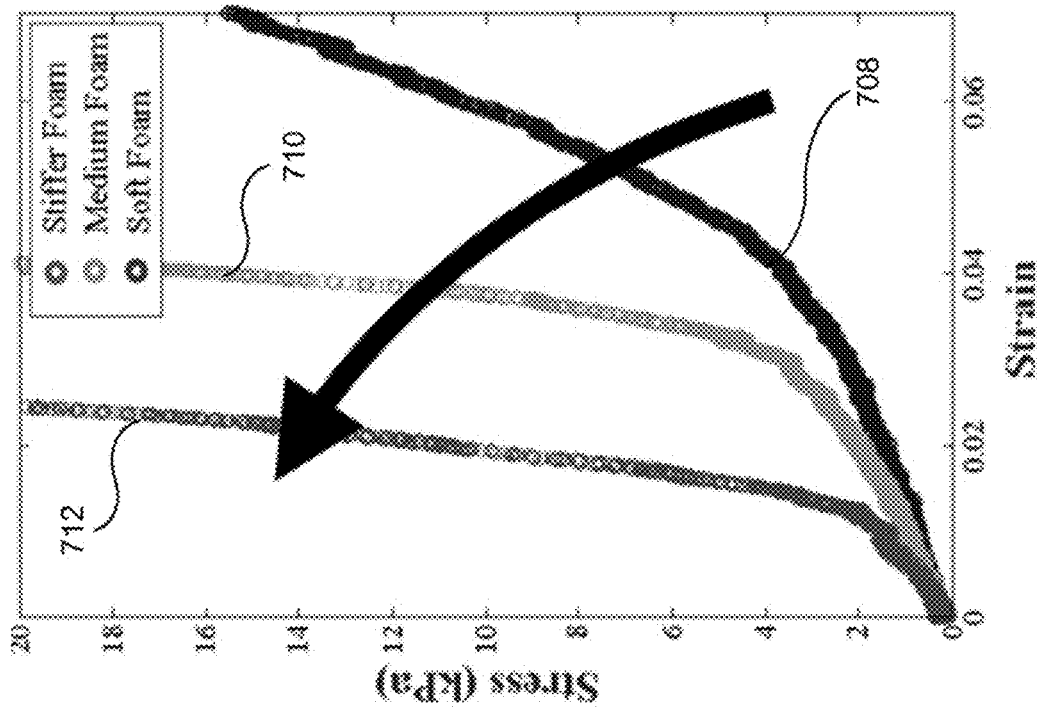
FIG. 7B is a graph of the stress-strain behavior of commercial foams at a strain rate of 0.1.
Figure 7A:
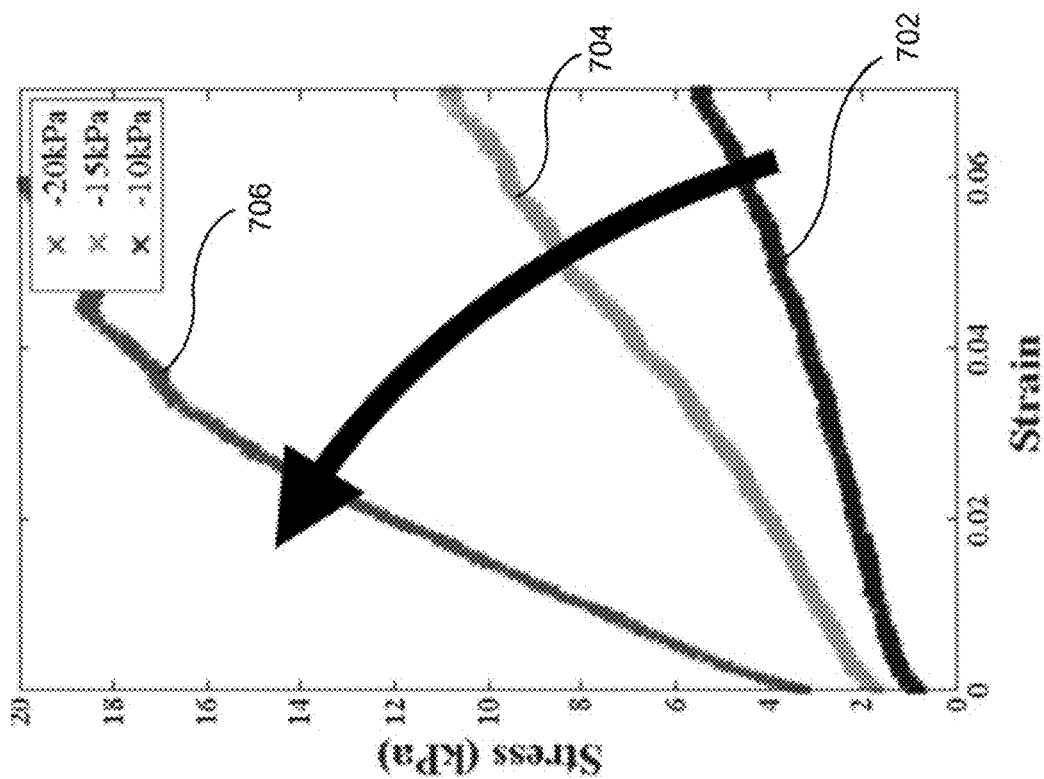
FIG. 7A is a graph of the stress-strain behavior of a granular orthosis at a strain rate of 0.1, according to an exemplary embodiment of the present disclosure.

A single granular orthosis prototype allowed one to adjust the negative pressure to match the range of material behaviors exhibited by multiple commercial foams. FIG. 7A is a graph of the stress-strain behavior of a granular orthosis prototype at a strain rate of 0.1, and FIG. 7B is a graph of the stress-strain behavior of commercial foams at a strain rate of 0.1. As can be seen in FIG. 7A, as the negative internal pressure of the granular orthosis devices increased from −10 kPa (702), to −15 kPa (704), and to −20 kPa (706), the devices showed a corresponding increase in stiffness. Generally, more negative pressure resulted in an increasing stiffness for the large volume fill prototypes. Other prototype configurations (e.g., small volume fills at both strain rates and large beads at slower strain rates) were not as predictable in terms of the negative pressure relationship. FIG. 7B shows the testing of a soft foam (708), a medium-stiffness foam (710), and a stiff foam (712). As can be seen in the stress-strain curve, and as would be expected for the foam materials, each foam comprised a densification strain at relatively low strains.

Figure 8:
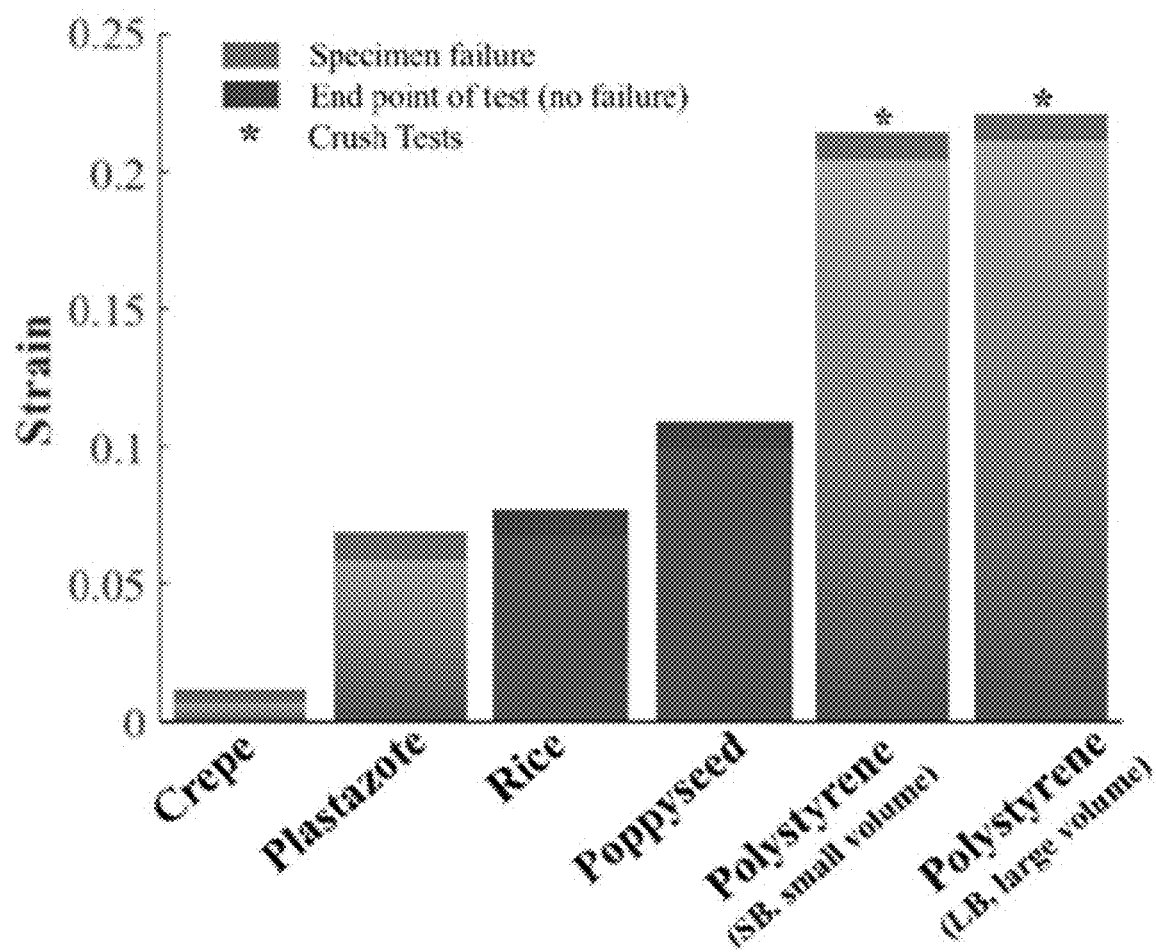
FIG. 8 is a graph showing the results of testing the maximum or failure strains reached for the granular orthosis prototypes and two common commercial foams.

FIG. 8 is a graph showing the results of testing the maximum or failure strains reached for the granular orthosis prototypes and two common commercial foams. The maximum or failure strains reached under standard testing protocols are shown with black bars; the strains reached under the crush testing protocols are shown with white bars. Under the standard protocol, specimens were compressed until either a predefined strain limit or time limit was reached. Crepe and Plastazote are shown as representatives of the foams with the minimum and maximum strains to failure, respectively. Crepe and Plastazote reached failure (densification, indicated by asterisks) whereas the granular orthosis prototypes did not. The granular orthosis prototypes were then compressed to failure under a crush protocol, reaching failure strains approximately 18 times greater than the minimum foam failure strain and 3 times greater than the maximum foam failure strain.

Figure 9:
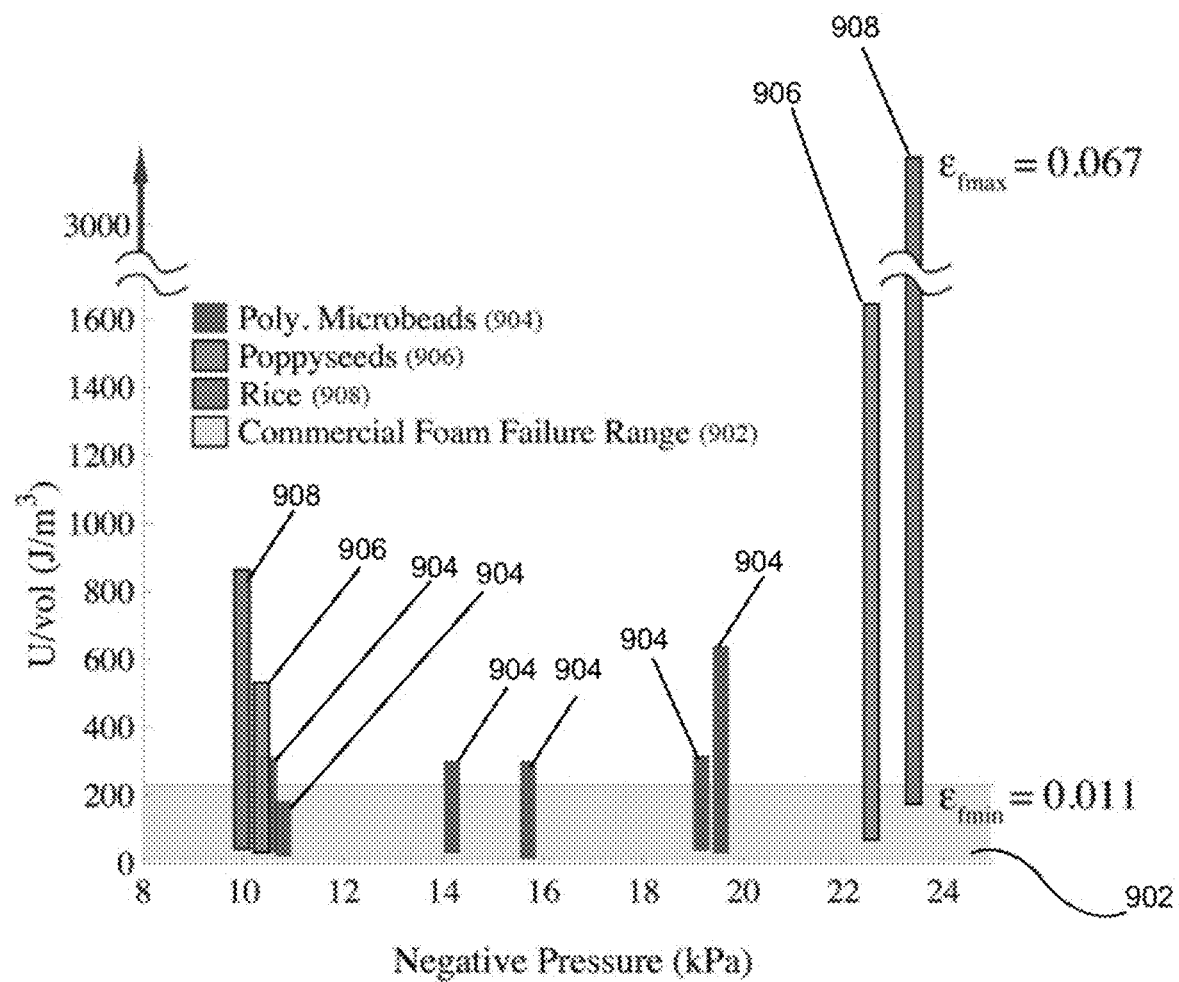
FIG. 9 is a graph of the minimum-maximum ranges of energy absorption of various granular orthosis prototype configurations at a strain rate of 0.001.

By adjusting negative pressure, each of the different prototype configurations was found to span the full range of energy absorptions observed of all the commercial foams tested at slow and fast strain rates. FIG. 9 is a graph of the minimum-maximum ranges of energy absorption of various granular orthosis prototype configurations at a strain rate of 0.001. Each bar depicts the range of energy absorbed (i.e., the first two regions 102,104 of FIG. 1) for each individual orthosis prototype compared to the minimum and maximum energy absorption values across all commercial foams tested (indicated by foam energy absorption performance band 902). The ranges of energy absorbed are obtained with respect to the minimum (0.011) and maximum (0.067) failure strains of the commercial foams tested. The results for polystyrene microbeads 904, poppyseeds 906, and rice 908 particulates are presented in the graph. At low strain rate, the polystyrene microbeads 904 have a range that extends from the low end to beyond the upper limit of the foam energy absorption performance band 902. The poppyseed 906 and rice 908 granules have a much larger range of energy absorptions. At higher negative pressure, the rice granule 908 prototype's energy absorption at the minimum failure strain is located near the upper limit of the foam energy absorption performance band 902. Its range then extends up to ~2800 $J/m^3$.

Figure 10:
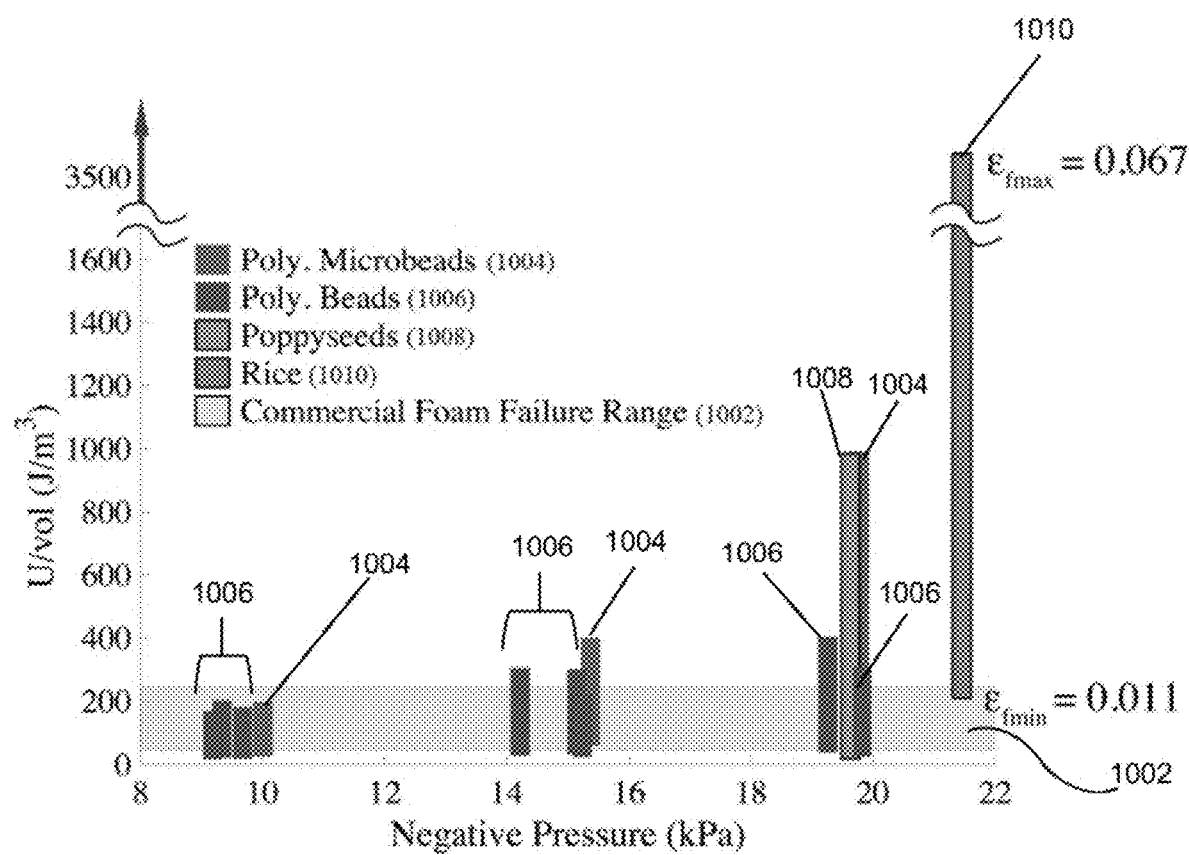
FIG. 10 is a graph of the minimum-maximum ranges of energy absorption of various granular orthosis prototype configurations at a strain rate of 0.1.

FIG. 10 is a graph of the minimum-maximum ranges of energy absorption of various granular orthosis prototype configurations at a strain rate of 0.1. Each bar depicts the range of energy absorbed for each individual orthosis prototype compared to the minimum and maximum energy absorption values across all commercial foams tested (indicated by foam energy absorption performance band 1002). The ranges of energy absorbed are obtained with respect to the minimum (0.011) and maximum (0.067) failure strains of the commercial foams tested. The results for polystyrene microbeads 1004, large-bead polystyrene beads 1006, poppyseeds 1008, and rice 1010 particulates are presented in the graph. At the higher strain rate, the energy absorption of the prototypes increased as the negative pressure increased. At low stiffness, the polystyrene microbead 1004 prototypes span approximately 75% of the foam energy absorption performance band 1002. The same prototypes span approximately 90% of the foam energy absorption performance band 1002 at high stiffness. At greater negative pressures (-20 kPa), the upper range of energy absorption for polystyrene microbead 1004 prototypes is much higher than at the smaller negative pressures. The large-bead polystyrene 1006 prototype ranges increase as stiffness increases, but not by as much as the microbeads 1004. The rice 1010 granule prototype range began near the upper limit of the foam energy absorption performance band 1002, and extended up to 3500 $J/m^3$.

A single variable-stiffness granular orthosis prototype is shown to exhibit a range of energy absorption characteristics, extending well beyond the range of the commercial foams tested. The energy absorption performance range of the polystyrene-filled prototypes increased with increasing negative pressure as the orthosis stiffness increased. In addition, this same trend occurred with rice and poppy seed prototypes. Rice and poppy seeds provide a much larger range of impact absorption behaviors than polystyrene (~3-5 times greater on average). Both rice and poppy seeds greatly exceed the foam energy absorption performance band defined by the performance of the commercial foams, signifying that there is potential for granular orthosis devices to mimic much stiffer materials. The negative pressure adjustment of a granular media within a single orthotic device can deliver a high level of control over its material properties.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

What is claimed is:

1. A system comprising:
   a first cell having an air impermeable outer bladder, the outer bladder defining a first internal pocket containing a plurality of first granular particulates, wherein the first cell is configured to maintain a first negative internal pressure relative to an area external to the outer bladder;
   a first valve in fluid communication with the first cell and the area external to the outer bladder, wherein the first valve extends from the first cell and through the outer bladder, and wherein the first valve is configured to provide fluid flow into and from the first cell to adjust the first negative internal pressure;
   a second cell adjacent to and at least partially coplanar with the first cell and having an air impermeable outer bladder, the outer bladder defining a second internal pocket containing a plurality of second granular particulates, wherein the second cell is configured to maintain a second negative internal pressure relative to an area external to the outer bladder; and
   a second valve in fluid communication with the second cell and the area external to the outer bladder, wherein the second valve extends from the second cell and through the outer bladder, and wherein the second valve is configured to provide fluid flow into and from the second cell to adjust the second negative internal pressure; wherein the plurality of first granular particulates are a different material than the plurality of second granular particulates.

2. The system of claim 1, wherein the first internal pocket comprises a plurality of third granular particulates, wherein the plurality of first granular particulates are a different material than the plurality of second granular particulates.

3. The system of claim 1, wherein the plurality of first granular particulates comprise a different geometry than the plurality of second granular particulates.

4. The system of claim 1, wherein the first negative internal pressure is a different pressure than the second negative internal pressure.

5. The system of claim 1, wherein the system forms part of an orthosis.

6. The system of claim 1, further comprising:
a fluid pump coupleable to the first valve; and
a controller configured to operate the fluid pump to adjust the first negative internal pressure to alter a stiffness of the first cell.

7. The system of claim 1, further comprising:
a fluid pump coupleable to the first and second valves; and
a controller configured to operate the fluid pump to adjust the first negative internal pressure to alter a stiffness of the first cell, the controller further configured to operate the fluid pump to adjust the second negative internal pressure to alter a stiffness of the second cell.

8. A method comprising:
providing a user-orthosis interface, the interface comprising:
a first cell having an air impermeable outer bladder; the first cell containing a plurality of first granular particulates;
a first valve in fluid communication with the first cell and an area external to the outer bladder, the first valve extending from the first cell and through the outer bladder, and wherein the first valve is configured to provide fluid flow into and from the first cell;
a second cell adjacent to and at least partially coplanar with the first cell and having an air impermeable outer bladder, the second cell containing a plurality of second granular particulates of a different material than the plurality of first granular particulates; and
a second valve in fluid communication with the second cell and an area external to the outer bladder, the second valve extending from the second cell and through the outer bladder, and wherein the second valve is configured to provide fluid flow into and from the second cell;
providing a pressure controller configured to attach to the first valve and the second valve and provide fluid into and remove fluid from the first cell and the second cell to adjust a first internal pressure of the first cell and a second internal pressure of the second cell;
removing fluid, via the pressure controller, from the first cell to decrease the first internal pressure; removing fluid, via the pressure controller, from the second cell to decrease the second internal pressure;
causing the plurality of first granular particulates to compact with each other to increase a stiffness of the first cell; and
causing the plurality of second granular particulates to compact with each other to increase a stiffness of the second cell such that the second cell has different material properties than the first cell based at least in part on the plurality of second granular particulates being a different material than the plurality of first granular particulates.

9. The method of claim 8, wherein the stiffness of the first cell is greater than the stiffness of the second cell.

10. The method of claim 8, wherein the plurality of first granular particulates comprise a different geometry than the plurality of second granular particulates.

11. The method of claim 8, wherein the interface is part of an orthotic insole, and wherein the orthotic insole is disposed within a shoe.

12. The method of claim 8,
wherein the interface is part of an orthotic insole,
wherein the orthotic insole is disposed within a shoe,
wherein the shoe comprises a first end and a second end,
wherein the first cell is proximate the first end of the shoe, and
wherein the second cell is proximate the second end of the shoe.

13. A method comprising:
providing an orthotic insole, the orthotic insole comprising:
a first cell having an air impermeable outer bladder, the outer bladder defining a first internal pocket containing a plurality of first granular particulates; and
a first valve providing fluid communication between the first internal pocket and an area external to the first cell;
a second cell adjacent to and at least partially coplanar with the first cell and having an air impermeable outer bladder, the outer bladder defining a second internal pocket containing a plurality of second granular particulates; and a second valve providing fluid communication between the first internal pocket and an area external to the second cell;
providing a pressure controller coupleable to the first valve and the second valve;
removing fluid, via the pressure controller, from the first cell to decrease a first internal pressure in the first cell relative to the area external to the first cell, wherein decreasing the first internal pressure causes the plurality of first granular particulates to compact and increases a stiffness of the first cell; and
removing fluid, via the pressure controller, from the second cell to decrease a second internal pressure in the second cell relative to the area external to the second cell, wherein decreasing the second internal pressure causes the plurality of second granular particulates to compact and increases a stiffness of the second cell, wherein the plurality of second granular particulates comprise a different material than the plurality of second granular particulates.

14. The method of claim 13, wherein the stiffness of the first cell is greater than the stiffness of the second cell.

15. The method of claim 13, wherein the plurality of first granular particulates have a different geometry than the plurality of second granular particulates.

16. The method of claim 13, wherein the orthotic insole and the pressure controller are disposed within a shoe.

\* \* \* \* \*